United States Patent
Zagury et al.

(10) Patent No.: US 6,878,370 B1
(45) Date of Patent: Apr. 12, 2005

(54) CHEMICALLY MODIFIED TNF-α

(75) Inventors: Daniel Zagury, Paris (FR); Jean-François Zagury, Paris (FR)

(73) Assignee: Neovacs, Paris (FR)

( * ) Notice: Subject to any disclaimer, the term of this patent is extended or adjusted under 35 U.S.C. 154(b) by 0 days.

(21) Appl. No.: 09/959,461

(22) PCT Filed: Apr. 20, 2000

(86) PCT No.: PCT/FR00/01043

§ 371 (c)(1), (2), (4) Date: Oct. 26, 2001

(87) PCT Pub. No.: WO00/64937

PCT Pub. Date: Nov. 2, 2000

(30) Foreign Application Priority Data

Apr. 26, 1999 (FR) .............................. 99 05258

(51) Int. Cl.$^7$ ....................... A61K 38/19; C07K 14/525
(52) U.S. Cl. ............................. 424/85.1; 514/2; 514/8; 514/12; 530/350
(58) Field of Search ................................. 530/350, 351; 514/2, 8, 12; 424/85.1, 85.2, 85.4

(56) References Cited

U.S. PATENT DOCUMENTS 4,414,147 A    11/1983    Klibanov et al.

FOREIGN PATENT DOCUMENTS

| FR | 2 677 654 A1 | 6/1991 |
| FR | 2 773 156 A1 | 12/1997 |
| WO | WO 94/21288 A1 | 9/1994 |
| WO | WO 94/21288 * | 9/1994 |

OTHER PUBLICATIONS

Tsunoda et al. (Mar. 1998), 56(3), pp. 573–578, Japanese Journal of clinical medicine.*

* cited by examiner

Primary Examiner—Prema Mertz
(74) Attorney, Agent, or Firm—Browdy and Neimark, PLLC

(57) ABSTRACT

The present invention concerns a chemically modified TNF-α, and a pharmaceutical composition and a vaccine composition containing the chemically modified TNF-α which are useful for combating overproduction of native TNF-α.

7 Claims, No Drawings

CHEMICALLY MODIFIED TNF-α

REFERENCE TO RELATED APPLICATIONS

The present application is the national stage under 35 U.S.C. §371 of international application PCT/FR00/01043, filed Apr. 20, 2000 which designated the United States, and which application was not published in the English language.

The present invention relates to new inactivated cytokines, which can be used for human immunisation.

PCT/FR92100544 has disclosed that it was possible to immunise man against cytokines after having inactivated them or inactivated native or homologous peptide fragments with an appropriate treatment preserving their immunogenicity. This document more specifically describes the chemical treatment of the cytokine or peptide or homologous fragment using an aldehyde or β propiolactone.

These compounds have proven to be very active. They have in particular been used within the scope of clinical trials on patients infected with HIV, and the latter have shown some clinical benefits (see A. Gringeri et al. J of AIDS 20: 358–370-1999).

But these compounds, prepared by treatment with formaldehyde, are sometimes difficult to produce, particularly with regard to stability and reproducibility.

The applicant has surprisingly discovered that some chemical treatments made it possible to obtain compounds possessing the same immunogenicity, in particular with a greater stability and reproducibility of preparation.

That is why a subject of the present application is a cytokine or cytokine fragment derivative of formula

$$Cy-(X-R)_n \qquad (I)$$

in which Cy represents a cytokine or a cytokine fragment, —(X—R) represents a free function of an amino acid constituting the cytokine or the cytokine fragment where X represents an NH group or a sulphur atom, n represents an integer from 1 to 70, and R represents a chemical group preserving for the said cytokine or said fragment sufficient immunogenic properties to create antibodies neutralising or blocking the said native cytokine and at the same time bringing about the loss of at least 90% of the biological properties of the said native cytokine, with the exception of the product of the reaction of a native cytokine with an aldehyde and carboxymethylated interferon-α.

In preferential conditions for the implementation of the above-described invention, R is a group which fixes itself to a thiol function and X represents a sulphur atom group.

R is thus preferably a carboxymethyl, carboxamide, N-alkylmaleimide, thionitrobenzoic group or a radical formed by reaction of a thiol function with ammonium 4-chloro-7-sulphobenzofurazane, N-[iodoethyl]-trifluoroacetamide r or N-(6-[7-amino-4-methylcoumarin-3-acetamido]hexyl)-3-(2'-pyridyldithio) propionamide.

Carboxymethylation blocks the cysteine residues, by adding a carboxymethyl radical (treatment of cytokine with iodoacetic acid, for example), carboxyamidination adds a carboxamide radical (treatment of the cytokine with iodoacetamide, for example), maleimidation adds an N-alkylmaleimide radical to the cysteines, for example N-ethylmaleimide (treatment of the cytokine with N-ethylmaleimide), Ellman's reaction adds a thionitrobenzoic radical to the cysteine (treatment of the cytokine with 5,5'-dithio-bis-[2-nitrobenzoic] acid or DTNB).

In other preferential conditions for the implementation of the above-described invention, R is a group which fixes itself to an amino function and X represents an NH group.

R is thus preferably a radical formed by reaction of an amino function with ethylacetimidate, an anhydride, 2-iminothiolane-HCl, N-succinimidyl S-acetylthioacetate, sulphosuccinimidyl-acetate, sulphosuccinimidyl-4-0-[4,4'-dimethoxytrityl]butyrate, succinimidyl 7-amino-4-methylcoumarin-3-acetate or sulphosuccinimidyl 7-amino-4-methylcoumarin-3-acetate or phenylglyoxal.

R advantageously has a molecular weight of between 10 and 2000, preferably between 20 and 1500, in particular between 30 and 1000, especially between 40 and 500.

R is preferably an organic radical as has been seen above.

The treatment of cytokine with ethylacetimidate produces the amidination of the amino functions. Citraconic anhydride can be mentioned as a useable anhydride.

As has been seen, other reagents can act on the amine functions such as for example Traut's reagent (treatment with 2-iminothiolane-HCl), by the addition of an SH protected by N-succinimidyl S-acetilthioacetate, or sulphosuccinimidyl-acetate or sulphosuccinimidyl-4-0-[4, 4'-dimethoxytrityl]butyrate, or also succinimidyl 7-amino-4-methylcoumarin-3-acetate or sulphosuccinimidyl 7-amino-4-methylcoumarin-3-acetate.

These chemical inactivations are achieved by a chemical modification of certain residues of the cytokine which blocks the biological function of the native cytokine. Preferably 50% of the above X groups above are modified, in particular 70%, especially all of them. The groups where X represents NH and those where X represents a sulphur atom, can be modified at the same time or preferably only one of these two groups. "n" can range up to 10 for example in the case where X represents a sulphur atom and for example up to 70 for example in the case where X represents NH.

The immunogenic compound according to the invention can be constituted by all or a fragment of the cytokine and can comprise, as is well known to a person skilled in the art, one or more modifications in the amino acids of this protein or fragment such as deletions, substitutions, additions, or functionalisations such as acylation of amino acids, in so far as these modifications remain within the framework specified above (absence of toxicity, immunological characteristics). For example, in general the replacement of a leucine residue by an isoleucine residue does not modify such properties. The modifications must generally concern less than 30% of the amino acids, preferably less than 20% and quite particularly less than 10%.

A fragment can comprise from 8 to 110 amino acids for example, preferably from 12 to 60 amino acids and in particular from 12 to 40 amino acids. Such a fragment can also comprise a C or N terminal side of from 1 to 5 supplementary amino acids that is to say different from the original segment.

Generally speaking, as far as modifications are concerned, the homology or the similarity between the modified immunogen and the cytokine a 10 or part of the native cytokine, as well as the dimensions of the immunogenic compound, as well as the methods of use, or coupling of the immunogenic compound according to the invention to an immunogenic protein such as tetanic toxoid, reference may be made in particular to WO-A-86/06 414 or EP-A-0.220.273 or PCT/US.86/00831, which are equivalents, the teaching of which is incorporated here by way of reference.

A subject of the present invention is also a preparation process for a cytokine or a fragment as described above, characterised in that the said cytokine or the said fragment is subjected to the action of a reagent capable of grafting an R group onto the said cytokine or the said fragment, in order to obtain the expected compound which is isolated.

As the examples described in the experimental part below and carried out on cytokines of human origin show, the new products obtained by these treatments, called "kinoids", have lost their natural biological activity, and are capable of inducing an immune response in mammals. In addition, the antibodies obtained by using these kinoids as immunogens recognise the non-inactivated native protein.

The examples cited refer to cytokines, IFNγ, TNFα, IL1, IL4, IL6, IL10, IL13 but these reactions can be applied to all the cytokines (interleukins—IL1, IL2, IL3 etc . . . , transforming growth factors—TGF-α and β, interferons, α, β, γ, τ (tau), tumor necrosis factors—TNF α and β, chemokines etc . . . ). The cytokine or a homologous peptide fragment can be produced by chemical synthesis or also by genetic engineering. By homologous peptide fragment is meant a peptide sequence which is sufficiently similar to the native cytokine to induce crossed antibodies which will neutralise the biological activity of the native cytokine. For example, the homologous peptide fragment can be a cytokine mutant prepared by genetic engineering. The advantage of chemical inactivation is that it will in addition make it possible to stabilise the molecule in order to obtain reproducible conformations and preparations.

In order to maximise the anti-cytokine immune response, the use of kinoids inactivated in a different manner and which can be complementary in terms of the immune reaction that they induce can be combined: for example a kinoid prepared by a method targeting the cysteines which can be combined with a kinoid prepared according to a method targeting the amine residues.

The kinoids can be combined to combat overproduction of cytokines, not only of kinoids of the same cytokine inactivated by different methods, but also kinoids of different cytokines overproduced in the same illness: for example in the case of AIDS immunisation can be carried out using combined kinoids IFNα and IFNγ, or in rheumatoid polyarthritis using kinoids IL1 and TNFα.

The compounds which are the subject of the present invention possess very beneficial pharmacological properties. They are particularly beneficial for active anti-cytokine immunisation in the case where illnesses are combined with an overproduction of these cytokines.

These properties are illustrated below in the experimental part. They justify the use of the compounds of formula (I) described above, as a medicament.

That is why a subject of the invention is also the compounds corresponding to formula I

$$Cy—(X—R)_n \quad (I)$$

in which Cy represents a cytokine or a cytokine fragment, —(X—R) represents a free function of an amino acid constituting the cytokine or the cytokine fragment where X represents an NH group or a sulphur atom, n represents an integer from 1 to 70, and R represents a chemical group, preserving for the said cytokine derivative or said fragment sufficient immunogenic properties to create antibodies neutralising or blocking the said native cytokine and at the same time bringing about the loss of at least 90% of the biological properties of the said native cytokine, for their use in a method of therapeutic treatment of the human or animal body, that is to say as a medicament.

The medicaments according to the present invention are used in treatments which are both curative and preventative. Generally speaking, they can be used in pathologies linked to an overproduction, or undesirable production of cytokine. For example, the TNFα kinoid can be used in active immunisation in rheumatoid polyarthritis where it has already been shown that the blocking of TNF by antibodies (passive immunisation) or soluble receptors limits the development of the illness, or also in cancers when there is overproduction of TNFα and cachexia. The kinoid IL1 can also be used in rheumatoid polyarthritis where there is an overproduction of IL1. The kinoid IFNγ can be used in AIDS where there is an overproduction of IFNγ: it can be used in multiple sclerosis where it has been shown that the administration of IFNγ leads to a worsening of the illness, or also in juvenile diabetes where it has been clearly shown on animal subjects and also by in situ studies in humans that the destruction of the islets of Langerhans is due to an overproduction of IFNγ. The kinoid IFNα can be used in AIDS where its overproduction has been clearly established and where the clinical benefit of anti-IFNα immunisation has been shown or also in lupus erythematous which has been shown to be able to be triggered by an injection of IFNα. The kinoid IL6 can be used in multiple myeloma or Castleman's disease or some melanomas where it has been shown that the cancerous cells proliferate thanks to IL6. The kinoids IL4 and IL13, isolated or together, can be used in cases of allergic pathologies where it has been shown that these cytokines are over-produced. All of these non-limiting examples show the wide range of uses of the kinoids described in this patent.

As in any active immunisation, the treatment can use only a fragment of cytokine inactivated by the methods mentioned above to stimulate the immune reaction which will neutralise the biological activity of the cytokine.

The immunogenic compounds according to the invention can be used as follows:

An immunogenic compound according to the present invention is administered to a patient, for example by subcutaneous or intramuscular route, in a sufficient quantity to be effective on a therapeutic level, to a subject in need of such a treatment. The dose administered can range for example from 20 to 1000 μg by intramuscular route in the form of w/o emulsion, once a month over three months, then periodically according to the level of the serum antibodies induced, for example every 2–6 months.

A composition according to the invention can be administered by any conventional route in use in the field of vaccines, in particular by subcutaneous route, by intramuscular route, by intravenous route or by oral route. The oromucous membrane or perriasal route can also be cited. Administration can take place in a single dose or be repeated one or more times after a certain time period.

A subject of the invention is also pharmaceutical compositions which contain at least one aforementioned compound, as an active ingredient.

In these compositions, the active ingredient is advantageously present in physiologically effective doses; the aforementioned compositions contain in particular an effective immunogenic dose of at least one active ingredient above. The immunogenic compound can be presented on its own or mixed with a pharmaceutically acceptable excipient such as an adjuvant.

These pharmaceutical compositions can in particular be liquids and can be presented in all the pharmaceutical forms currently used in human medicine for vaccines, such as for example injectable preparations in particular in the form of an emulsion; they are prepared according to the usual methods. The active ingredient(s) can be incorporated into excipients normally used in these pharmaceutical compositions, such as aqueous vehicles, calcium phosphate, alum . . .

A subject of the present invention is also a preparation process for an above-described composition, characterised in that the active ingredient(s) is mixed, according to methods known per se, with acceptable, in particular pharmaceutically acceptable, excipients.

Finally, a subject of the invention is the use of a cytokine or a cytokine fragment of formula $$Cy-(X-R)_n \qquad (I)$$

in which Cy represents a cytokine or a cytokine fragment, —(X—R) represents a free function of an amino acid constituting the cytokine or the cytokine fragment where X represents an NH group or a sulphur atom, n represents an integer from 1 to 70, and R represents a chemical group preserving for the said cytokine or said fragment sufficient immunogenic properties to create antibodies neutralising or blocking the said native cytokine and at the same time bringing about the loss of at least 90% of the biological properties of the said native cytokine, in order to obtain a medicament intended to combat the overproduction of these native cytokines.

In addition a subject of the invention is a kit comprising a pharmaceutical vaccine composition which in addition to the active ingredient (for example cytokine or cytokine fragment) can comprise an adjuvant and/or another immunogen with the anti-overproduction properties in respect of these native cytokines.

Preferential conditions for the use of the cytokines or cytokine fragments described above apply equally to the other subjects of the invention mentioned above.

The following examples illustrate the present application.

EXAMPLE 1

Treatment of IFNγ by Maleimidation 10 mg of human recombinant IFNγ was placed in solution at 0.5 mg per ml in 0.1 M pH 7 phosphate buffer. 1 mg of N-ethylmaleimide was added to this solution. After 1 hour of reaction, the solution was dialysed against pH 7.2 PBS. The analysis of the kinoid with acrylamide gel shows the same 17 KD band compared with the native IFNγ.

EXAMPLE 2

Loss of the Biological Activity of the Inactivated IFNγ by Maleimidation

The kinoid IFNγ was then tested to evaluate its biological activity. There are several biological activity tests for IFNγ. Tests for apoptosis induction, tests for induction of surface antigens such as MHC (major histocompatibility complex), but also testing for an antiviral effect on MDBK cells.

The aim of the antiviral effect measurement test is to evaluate the inhibition of the lysis of MDBK cells in the presence of IFNγ. This test is very sensitive and makes it possible to measure IFNγ picograms.

Freshly trypsinated MDBK cells are grown in RPMI medium, 5% foetal calf serum, at a concentration of 30 000 cells per well. After at least 6 hours, the cells are washed in RPMI, then 50 ml of IFNγ is added, diluted in RPMI in a series of ½ dilutions. The plate is then incubated at 37° C. 5% $CO_2$ over 18 to 24 hours.

After 18 to 24 hours, the supernatant of each well is removed, the cells are washed and 100 ml containing 100 LD50 (lethal dose 50%) of VSV virus diluted in RPMI is added. The plate is left to incubate over 18 to 36 hours. The lytic effect of the virus is measured under the microscope and makes it possible to quantify (scale 1 to 4) from which dilution the lysis operates.

In order to test the activity of the kinoid compared with the native IFNγ, solutions containing 100 ng/ml of these molecules are used. The following result is obtained:

|  | Native IFNγ | Maleimidated kinoid IFNγ |
| --- | --- | --- |
| Positive antiviral effect | Up to a dilution of $2^{10}$ | Up to a dilution of $2^2$ |

The kinoid has thus lost its antiviral activity and is inactive at a factor greater than $2^8$ in these conditions, which corresponds to an inactivation greater than 99%.

EXAMPLE 3

Immunogenicity of the Maleimidated IFNγ

Kinoids prepared according to example 1 were used to immunise mice. The immunisation procedure is that which is traditionally used: injection into mice by intramuscular route (im), of 100 ml of emulsion (1:1) in Freund's complete adjuvant containing 20 mg of product at day 0, with a 5 mg Freund's incomplete adjuvant booster on days 21 and 35. The serum from the mice is sampled on days −2 and 40 and analysed by ELISA on plates sensitised with the native protein (not chemically treated) and with kinoid. The sera were tested at a dilution of 1/500.

The results expressed as optical density, obtained from 3 immunised mice (1 to 3) and 3 non-immunised mice (4 to 6), are given in the following table:

|  |  | Native protein | Kinoid |
| --- | --- | --- | --- |
| Mouse 1 | D-2 | 0.1 | 0.2 |
|  | D40 | 1.8 | 2.1 |
| Mouse 2 | D-2 | 0.15 | 0.2 |
|  | D40 | 1.5 | 2.2 |
| Mouse 3 | D-2 | 0.3 | 0.1 |
|  | D40 | 2 | 2.1 |
| Mouse 4 | D-2 | 0.2 | 0.15 |
|  | D40 | 0.2 | 0.1 |
| Mouse 5 | D-2 | 0.15 | 0.2 |
|  | D40 | 0.1 | 0.15 |
| Mouse 6 | D-2 | 0.15 | 0.2 |
|  | D40 | 0.2 | 0.1 |

These results show that the mice immunised by the kinoid produce antibodies capable of recognising the native protein and the kinoid in the same fashion. Furthermore, this confirms the non-toxicity of immunisation with kinoids as the mice tolerated the immunisation very well.

EXAMPLE 4

Treatment of TNFα by Carboxamidination 3 mg of TNFα dissolved in 2 ml of 0.3 M Tris buffer, 6 M guanidine, 10 mM EDTA, 1 mM DTT were treated with 107 ml of a 0.5 M iodacetamide solution under a nitrogen barrier for 1 hour and 30 minutes at 37° C. After stopping the reaction by adding 2.5 ml of β-mercaptoethanol, the reaction mixture was dialysed successively against 8 M, 4M, 2 M urea and against phosphate buffer (PBS).

EXAMPLE 5

Loss of Biological Activity of the TNFα Prepared by Carboxamidination

There are several tests for measuring the cytotoxic activity of TNFα on cell lines, whether it is the L929 mouse line or the WEHI164 line. The principle of the test on the line WEHI 164 is that the TNFα will induce a cell lysis measured by crystal violet.

50 000 cells are placed in wells of 96-well Costar plates, in 100 ml of 10% RPMI FCS. They are left to rest for 4 hours at 37° C. Three times 100 ml of RPMI containing increasing dilutions of native or inactivated TNFα are then added to these wells. The dilutions are carried out 5 by 5. After 24 hours at 37° C., the supernatant is removed and the cells are fixed in each well with 200 ml of methanol for 30 seconds. After having removed the methanol crystal violet is added in a 1% solution over 10 minutes. The wells are then washed with distilled water, then the plate is allowed to dry by turning it over onto absorbent paper. After drying marking is measured at 620 nm in a plate reader.

The percentage lysis is calculated using the formula:

$$\% = (OD_{max} - OD_{exp})/(OD_{max} - OD_{min}) \times 100$$

where max corresponds to the absence of lysis (control RPMI on its own) and min corresponds to maximum lysis (HCl or excess native TNFα).

The results (% lysis) obtained for native TNFα and inactivated TNFα according to example 4 are the following:

| Quantity/well: | Native TNFα | Inactivated TNFα |
|---|---|---|
| 10 mg | 100% | 5% |
| 1 mg | 100% | 0% |
| 100 ng | 100% | 5% |
| 10 ng | 100% | 2% |
| 1 ng | 100% | 0% |
| 100 pg | 98% | 3% |
| 10 pg | 65% | 2% |
| 1 pg | 5% | 4% |

It can be seen that, whatever the doses of inactivated TNFα, it no longer has a lytic effect on the cells (background noise), while the native TNFα is active up to a dilution up to factor of $10^5$ compared with the initial dilution.

EXAMPLE 6

Immunogenicity of the Carboxamided TNFα

Kinoids prepared according to example 4 were used to immunise mice. The immunisation procedure is that which is traditionally used: injection into mice (in im), of 100 ml of emulsion (1:1) in Freund's complete adjuvant containing 20 mg of product at day 0, with a 5 mg Freund's incomplete adjuvant booster on days 21 and 35. The serum from the mice is sampled on days −2 and 40 and analysed by ELISA on plates sensitised with the native protein (not chemically treated) and with kinoid. The sera were tested at a dilution of 1/500.

The results expressed as optical density, obtained from 3 immunised mice (1 to 3) and 3 non-immunised mice (4 to 6), are given in the following table:

|  |  | Native protein | Kinoid |
|---|---|---|---|
| Mouse 1 | D-2 | 0.1 | 0.15 |
|  | D40 | 1.9 | 1.7 |
| Mouse 2 | D-2 | 0.1 | 0.2 |
|  | D40 | 1.7 | 2 |
| Mouse 3 | D-2 | 0.2 | 0.2 |
|  | D40 | 1.8 | 1.8 |
| Mouse 4 | D-2 | 0.2 | 0.3 |
|  | D40 | 0.1 | 0.1 |
| Mouse 5 | D-2 | 0.2 | 0.2 |
|  | D40 | 0.15 | 0.2 |
| Mouse 6 | D-2 | 0.15 | 0.2 |
|  | D40 | 0.2 | 0.15 |

These results show that the mice immunised with the kinoid produce antibodies capable of recognising the native protein and the kinoid in the same fashion. Furthermore, this confirms the non-toxicity of the immunisation with the kinoids as the mice tolerated the immunisation very well.

EXAMPLE 7

Treatment of the IL4 with Elimar's Reagent 1 mg of IL4 in 0.1 M phosphate buffer pH 8.0 was treated with 4 mg of DTNB for 30 minutes at ambient temperature, away from the light. The mixture was then dialysed against PBS.

EXAMPLE 8

Loss of Biological Activity of the IL4 Treated with Ellman's Reagent

IL4 has several effects on the activation-differentiation of B-lymphocytes with induction of expression of surface markers such as class II MHC, CD40, CD23 which can be evaluated by cytofluorometry. In the present experiment, the proliferation of mononucleated cells in the peripheral blood (PBMCs) activated by phytohemagglutinin (PHA) and IL2, in the presence of different concentrations of IL4, is calculated.

The PBMCs are purified on a Ficoll gradient. 5 million cells are placed in a flask in 5 ml of RPMI, FCS %, with an addition of PHA 1/1000 and culture is continued over 48 hours at 37° 5% $CO_2$. IL2 is then added at a concentration of 20 Ul/ml, and after 48 hours, the cells are centrifuged, washed and concentrated at 20 000 cells per well in a 96-well culture plate in the presence of RPMI, 5% foetal calf serum (FCS), PHA 1/1000. To these wells are added different quantities of IL4 diluted with RPMI. The plates are then incubated for 40 hours, then tritiated thymidine is added to them, and after 6 hours, the cell proliferation is measured by evaluating the incorporation of labelled thymidine in a β counter.

The proliferation results (cpm) obtained in the presence of IL4 native or inactivated according to example 7 are the following:

| Quantity per well: | Native IL4 | Inactivated IL4 |
|---|---|---|
| 100 ng | 49 000 | 400 |
| 10 ng | 25 000 | 300 |
| 1 ng | 6 000 | 400 |
| 0.1 ng | 1 000 | 300 |

It can be seen that inactivation is effective even after dilution to a factor of 1000, which shows biological inactivation of more than 99.9%.

EXAMPLE 9

Immunogenicity of the IL4 Inactivated by Ellman's Reagent

Kinoids prepared according to example 7 were used to immunise mice. The immunisation procedure is that which is traditionally used: injection into mice (in im), of 100 ml of emulsion (1:1) in Freund's complete adjuvant containing 20 mg of product at day 0, with a 5 mg Freund's incomplete adjuvant booster on days 21 and 35. The serum from the mice is sampled on days −2 and 40 and analysed by ELISA on plates sensitised with the native protein (not chemically treated) and with kinoid. The sera were tested at a dilution of 1/500.

The results expressed as optical density, obtained from 3 immunised mice (1 to 3) and 3 non-immunised mice (4 to 6), are given in the following table:

|         |     | native protein | kinoid |
|---------|-----|----------------|--------|
| Mouse 1 | D-2 | 0.2            | 0.1    |
|         | D40 | 2              | 1.9    |
| Mouse 2 | D-2 | 0.3            | 0.15   |
|         | D40 | 2.1            | 1.9    |
| Mouse 3 | D-2 | 0.3            | 0.2    |
|         | D40 | 2.1            | 1.9    |
| Mouse 4 | D-2 | 0.15           | 0.2    |
|         | D40 | 0.1            | 0.25   |
| Mouse 5 | D-2 | 0.1            | 0.15   |
|         | D40 | 0.2            | 0.2    |
| Mouse 6 | D-2 | 0.1            | 0.1    |
|         | D40 | 0.15           | 0.3    |

These results show that the mice immunised with the kinoid produce antibodies capable of recognising the native protein and the kinoid in the same way. Furthermore, it confirms the non-toxicity of immunisation with kinoids as the mice tolerated the immunisation very well.

EXAMPLE 10

Treatment of the IL6 by Amidination 40 ml of a 12.5 mg/ml ethylacetimidate solution in 5 N NaOH is added, accompanied by stirring, to 4 ml of a 1 mg/ml IL6 solution in 0.1 M borate buffer, pH 8.5 cooled in an ice bath. The mixture is stirred for 30 to 60 minutes in the ice bath keeping the pH at 8.5 by adding 0.1N NaOH, after which the mixture is dialysed against PBS.

EXAMPLE 11

Loss of Biological Activity of the IL6 Treated by Amidination

The test to measure the activity of IL6 rests on the measurement of the proliferation of a cell line dependant on IL6 for its growth. 7TD1 cells are cultured in the following culture medium: Dulbecco-modified Eagle medium (DMEM) with 10% foetal calf serum, 1.5 mM glutamine, 0.24 mM asparagine, 0.55 mM arginine, 50 mM P-mercaptoethanol, 0.1 mM hypoxanthine and 16 mM thymidine. These cells are normally cultured in the presence of native IL6 at a concentration of 200 U/ml i.e. in the order of 1 ng/ml of IL6.

The cells are washed twice in DMEM medium alone and resuspended in the culture medium at a concentration of 20 000 cells per ml. 100 ml of these cells are added to diluted IL6 (in the same volume of 100 ml) or sample to be tested.

After incubation for 3 to 4 days at 37° C. and 8% $CO_2$, the number of living cells is evaluated by colorimetry, measuring the level of hexosamimidase (Landegren et al., J immunol Methods, 67, 379, 1984): for this, the microplates are centrifuged, the cells are washed twice in PBS in order to remove the serum, the colouring substrate is added (1 volume of 7.5 mM p-nitrophenyl-N-acetyl-b-D-glucosaminide, 0.1 M sodium citrate pH 5, 1 volume of 0.5% Triton X100) at 60 ml per well. After incubation for 4 hours at 37° C., the visualizing agent is added (0.1 M glycine-NaOH, pH 10.4). The colour is read under 405 nm absorbance with a blank control at 620 nm.

One unit of IL6 corresponds to 50% of the maximum proliferation obtained according to the following calculation:

Max prolif 50=control prolif+½ (max prolif-control prolif).

In the case of the preparations of example 10, 5 ng of preparation in 100 ml was tested each time, and 3 by 3 dilutions carried out. The dilutions giving one unit are given in the following table:

|            | Dilution to obtain 1 unit | % inactivation |
|------------|---------------------------|----------------|
| Native IL6 | $3^6$                     | 0%             |
| IL6 kinoid | 3                         | 99.8           |

These results show the disappearance of IL6 biological activity at more than 99.8% in the IL6 kinoid inactivated by amidination compared to native IL6.

EXAMPLE 12

Immunogenicity of the IL6 Inactivated by Amidination

Kinoids prepared according to example 10 were used to immunise mice. The immunisation procedure is that which is traditionally used: injection into mice (in im), of 100 ml of emulsion (1:1) in Freund's complete adjuvant containing 20 mg of product at day 0, with a 5 mg Freund's incomplete adjuvant booster on days 21 and 35. The serum from the mice is sampled on days −2 and 40 and analysed by ELISA on plates sensitised with the native protein (not chemically treated) and with kinoid. The sera were tested at a dilution of 1/500.

The results expressed as optical density, obtained from 3 immunised mice (1 to 3) and 3 non-immunised mice (4 to 6), are given in the following table:

|         |     | Native protein | Kinoid |
|---------|-----|----------------|--------|
| Mouse 1 | D-2 | 0.15           | 0.2    |
|         | D40 | 1.7            | 1.9    |
| Mouse 2 | D-2 | 0.1            | 0.1    |
|         | D40 | 1.9            | 1.6    |
| Mouse 3 | D-2 | 0.25           | 0.15   |
|         | D40 | 1.9            | 2      |
| Mouse 4 | D-2 | 0.1            | 0.1    |
|         | D40 | 0.15           | 0.1    |
| Mouse 5 | D-2 | 0.2            | 0.3    |
|         | D40 | 0.3            | 0.2    |
| Mouse 6 | D-2 | 0.2            | 0.15   |
|         | D40 | 0.1            | 0.1    |

These results show that the mice immunised with the kinoid produce antibodies capable of recognising the native protein and the kinoid in the same fashion. Furthermore, it confirms the non-toxicity of the immunisation with the kinoids as the mice tolerated the immunisation very well.

EXAMPLE 13

Treatment of the IL10 by Reductive Alkylation 1.5 mg of sodium borohydride in powder form was added accompanied by stirring to 3 ml of IL10 at a concentration of 1 mg/ml in 0.2 M borate buffer pH 9. A 37% formaldehyde solution was added to this solution in 5 successive portions of 15 ml over a period of 30 minutes. The reaction medium was dialysed at the end of this period against PBS.

EXAMPLE 14

Loss of Biological Activity of IL10 Inactivated by Reductive Alkylation

The IL10 has a proliferative action on the cells of the mastocyte mouse line MC/9. MC/9 cells are cultured in RPMI, 10% FCS, 2 mM L-glutamine, 0.05 mM β-mercaptoethanol, 100 U/ml of GM-CSF at the initial concentration of 2 $10^5$/ml. After 2 days the cells are washed and resuspended at 2 $10^5$/ml in RPMI, 10% FCS.

100 ml of cells are placed in wells of 96-well culture microplates. To these wells are added 100 ml of IL10 native or inactivated according to example 13 at different dilutions. The cells are cultured over 40 hours, then tritiated thymidine is added and after 8 hours the cell DNA is caught on a filter (MASH, Coulter) and the cell proliferation is evaluated in a β counter.

The proliferation results (cpm) obtained are the following, in relation to the quantity of IL10 poured into each well:

| Quantity per well: | Native IL10 | IL10 kinoid |
|---|---|---|
| 100 ng | 98 000 | 1 600 |
| 10 ng | 88 000 | 900 |
| 1 ng | 36 000 | 1200 |
| 100 pg | 6 000 | 1000 |
| 10 pg | 1 000 | 800 |
| control (no IL10) | 1100 | 1100 |

These results clearly show that the IL10 kinoid was effectively inactivated by the reductive alkylation.

EXAMPLE 15

Immunogenicity of the IL10 Inactivated by Reductive Alkylation

Kinoids prepared according to example 13 were used to immunise mice. The immunisation procedure is that which is traditionally used: injection into mice (in im), of 100 ml of emulsion (1:1) in Freund's complete adjuvant containing 20 mg of product at day 0, with a 5 mg Freund's incomplete adjuvant booster on days 21 and 35. The serum from the mice is sampled on days −2 and 40 and analysed by ELISA on plates sensitised with the native protein (not chemically treated) and with kinoid. The sera were tested at a dilution of 1/500.

The results expressed as optical density, obtained from 3 immunised mice (1 to 3) and 3 non-immunised mice (4 to 6), are given in the following table:

|  |  | Native protein | Kinoid |
|---|---|---|---|
| Mouse 1 | D-2 | 0.2 | 0.15 |
|  | D40 | 2 | 2.1 |
| Mouse 2 | D-2 | 0.15 | 0.3 |
|  | D40 | 1.5 | 1.8 |
| Mouse 3 | D-2 | 0.2 | 0.1 |
|  | D40 | 1.9 | 1.7 |
| Mouse 4 | D-2 | 0.1 | 0.1 |
|  | D40 | 0.1 | 0.15 |
| Mouse 5 | D-2 | 0.15 | 0.25 |
|  | D40 | 0.1 | 0.1 |
| Mouse 6 | D-2 | 0.2 | 0.2 |
|  | D40 | 0.1 | 0.25 |

These results show that the mice immunised with the kinoid produce antibodies capable of recognising the native protein and the kinoid in the same manner. Furthermore, this confirms the non-toxicity of the immunisation with the kinoids as the mice tolerated the immunisation very well.

EXAMPLE 16

Inactivation of the IFNγ by an Anhydride

A solution of 1M maleic anhydride in redistilled dioxane was added to IFNγ in 0.1 M phosphate buffer, pH 8.1 at a concentration of 1 mg per ml, cooled in an ice bath. The addition is carried out, accompanied by stirring, in small fractions at 5 minute intervals, whilst keeping the pH at 8.0 by adding 0.05 N NaOH throughout the reaction time. The reaction was stopped by dialysis against PBS after stirring was continued for a further 30 minutes.

EXAMPLE 17

Immunogenicity of the IFNα Inactivated by an Anhydride

Kinoids prepared according to example 16 were used to immunise mice. The immunisation procedure is that which is traditionally used: injection into mice (in im), of 100 ml of emulsion (1:1) in Freund's complete adjuvant containing 20 mg of product at day 0, with a 5 mg Freund's incomplete adjuvant booster on days 21 and 35. The serum from the mice is sampled on days −2 and 40 and analysed by ELISA on plates sensitised with the native protein (not chemically treated) and with kinoid. The sera were tested at a dilution of 1/500.

The results expressed as optical density, obtained from 3 immunised mice (1 to 3) and 3 non-immunised mice (4 to 6), are given in the following table:

|  |  | Native protein | Kinoid |
|---|---|---|---|
| Mouse 1 | D-2 | 0.3 | 0.2 |
|  | D40 | 2.2 | 1.9 |
| Mouse 2 | D-2 | 0.2 | 0.1 |
|  | D40 | 1.9 | 1.7 |
| Mouse 3 | D-2 | 0.15 | 0.25 |
|  | D40 | 1.9 | 2.1 |
| Mouse 4 | D-2 | 0.15 | 0.1 |
|  | D40 | 0.1 | 0.25 |
| Mouse 5 | D-2 | 0.25 | 0.1 |
|  | D40 | 0.15 | 0.15 |
| Mouse 6 | D-2 | 0.1 | 0.2 |
|  | D40 | 0.15 | 0.1 |

These results show that the mice immunised with the kinoid produce antibodies capable of recognising the native protein and the kinoid in the same fashion. Furthermore, it confirms the non-toxicity of immunisation with kinoids as the mice tolerated the immunisation very well.

EXAMPLE 18

Treatment of the IL13 with p-hydroxyphenylglyoxal 100 ml of a 20 mg/ml solution of hydroxyphenylglyoxal was added to a 1 mg/ml solution of IL13 in PBS, in the same buffer per ml of IFNγ solution. The reaction was continued for 1 hour at a temperature of 37° C., and the reaction medium was dialysed against PBS.

EXAMPLE 19

Loss of Biological Activity of the IL13 Treated with p-hydroxyphenylglyoxal

The IL13 has a proliferative activity on the erythroleucemic human cell line TF-1. As in the previous experiments, the TF-1 cells were cultured in RPMI, 5% FCS, then distributed onto microplates at $10^4$ cells per well in 100 ml. Increasing dilutions of IL13, native or inactivated according to example 18, are added to these wells. After 40 hours, tritiated thymidine is added.

After 8 hours, the DNA from the cells is collected on a filter (MASH, Coulter) and then the radioactivity is measured with a β counter.

The proliferation results (in cpm) obtained with the IL13 are the following:

| Quantity added per well | native IL13 | IL13 kinoid |
| --- | --- | --- |
| 100 ng | 76000 | 2000 |
| 10 ng | 80000 | 1200 |
| 1 ng | 62000 | 900 |
| 100 pg | 21000 | 700 |
| 10 pg | 3000 | 1100 |
| control | 900 | 900 |

It can be seen that the inactivation was effective since the native IL13 diluted $10^4$ times (10 pg) is more active than the non-diluted kinoid at the same initial concentration (100 ng).

EXAMPLE 20

Immunogenicity of the IL13 Inactivated by p-hydroxyphenylglyoxal

Kinoids prepared according to example 18 were used to immunise mice. The immunisation procedure is that which is traditionally used: injection into mice (in im), of 100 ml of emulsion (1:1) in Freund's complete adjuvant containing 20 mg of product at day 0, with a 5 mg Freund's incomplete adjuvant booster on days 21 and 35. The serum from the mice is sampled on days −2 and 40 and analysed by ELISA on plates sensitised with the native protein (not chemically treated) and with kinoid. The sera were tested at a dilution of 1/500.

The results expressed as optical density, obtained from 3 immunised mice (1 to 3) and 3 non-immunised mice (4 to 6), are given in the following table:

|  |  | Native protein | Kinoid |
| --- | --- | --- | --- |
| Mouse 1 | D-2 | 0.3 | 0.25 |
|  | D40 | 1.8 | 1.8 |
| Mouse 2 | D-2 | 0.2 | 0.15 |
|  | D40 | 2.1 | 2 |
| Mouse 3 | D-2 | 0.35 | 0.15 |
|  | D40 | 2 | 1.8 |
| Mouse 4 | D-2 | 0.3 | 0.1 |
|  | D40 | 0.1 | 0.1 |
| Mouse 5 | D-2 | 0.1 | 0.25 |
|  | D40 | 0.2 | 0.15 |
| Mouse 6 | D-2 | 0.2 | 0.1 |
|  | D40 | 0.3 | 0.15 |

These results show that the mice immunised with the kinoid produce antibodies capable of recognising the native protein and the kinoid in the same fashion. Furthermore, it confirms the non-toxicity of the immunisation with the kinoids as the mice tolerated the immunisation very well.

EXAMPLE 21

Inactivation of the IL4 by Reductive Alkylation 1 mg of sodium borohydride and, immediately afterwards 50 ml of 37% formaldehyde solution were added accompanied by stirring in 5 successive fractions at 5 minute intervals to a solution of IL4 at a concentration of 1 mg/ml (5 ml) in 0.2 M borate buffer at pH 9. After the last addition of the aldehyde, the mixture was stirred for a further 15 minutes before being dialysed against PBS.

The same test was carried out as that described in example 8 to measure the inactivation of the IL4 kinoid by reductive alkylation. The result obtained was similar to that of example 8 as the cells stimulated by native IL4 proliferated and not the cells stimulated by the kinoid.

EXAMPLE 22

Immunogenicity of the IL4 Inactivated by Reductive Alkylation

Kinoids prepared according to example 21 were used to immunise mice. The immunisation procedure is that which is traditionally used: injection into mice (in im), of 100 ml of emulsion (1:1) in Freund's complete adjuvant containing 20 mg of product at day 0, with a 5 mg Freund's incomplete adjuvant booster on days 21 and 35. The serum from the mice is sampled on days −2 and 40 and analysed by ELISA on plates sensitised with the native protein (not chemically treated) and with kinoid. The sera were tested at a dilution of 1/500.

The results expressed as optical density, obtained from 3 immunised mice (1 to 3) and 3 non-immunised mice (4 to 6), are given in the following table:

|  |  | Native protein | Kinoid |
| --- | --- | --- | --- |
| Mouse 1 | D-2 | 0.25 | 0.2 |
|  | D40 | 1.7 | 2 |
| Mouse 2 | D-2 | 0.1 | 0.15 |
|  | D40 | 1.8 | 1.8 |
| Mouse 3 | D-2 | 0.1 | 0.2 |
|  | D40 | 2 | 1.9 |

-continued

|  |  | Native protein | Kinoid |
|---|---|---|---|
| Mouse 4 | D-2 | 0.25 | 0.1 |
|  | D40 | 0.15 | 0.2 |
| Mouse 5 | D-2 | 0.2 | 0.2 |
|  | D40 | 0.3 | 0.1 |
| Mouse 6 | D-2 | 0.1 | 0.1 |
|  | D40 | 0.15 | 0.1 |

These results show that the mice immunised with the kinoid produce antibodies capable of recognising the native protein and the kinoid in the same fashion. Furthermore, it confirms the non-toxicity of immunisation with kinoids as the mice tolerated the immunisation very well.

EXAMPLE 23

Inactivation of the TNFα with Ethylacetimidate.

50 ml of an ethylacetimidate solution, and HCl at 12.5 mg/ml in 5N NaOH cooled in an ice bath were added, accompanied by stirring to 2 ml of a 1 mg/ml solution of IFNα in 0.1 M borate buffer. The reaction was continued for 1 hour at 0° C., accompanied by stirring, keeping the pH at 8.5 by adding diluted NaOH. The reaction was stopped by dialysis against PBS.

The inactivation of the TNFα obtained was evaluated according to the same test as that described in example 5. The results were similar and there was no longer lysis of the cells in the presence of the kinoid.

EXAMPLE 24

Immunogenicity of the TNFα Inactivated with Ethylacetimidate

Kinoids prepared according to example 23 were used to immunise mice. The immunisation procedure is that which is traditionally used: injection into mice (in im), of 100 ml of emulsion (1:1) in Freund's complete adjuvant containing 20 mg of product at day 0, with a 5 mg Freund's incomplete adjuvant booster on days 21 and 35. The serum from the mice is sampled on days –2 and 40 and analysed by ELISA on plates sensitised with the native protein (not chemically treated) and with kinoid. The sera were tested at a dilution of 1/500.

The results expressed as optical density, obtained from 3 immunised mice (1 to 3) and 3 non-immunised mice (4 to 6), are given in the following table:

|  |  | Native protein | Kinoid |
|---|---|---|---|
| Mouse 1 | D-2 | 0.1 | 0.2 |
|  | D40 | 2.1 | 2 |
| Mouse 2 | D-2 | 0.1 | 0.2 |
|  | D40 | 2 | 2.2 |
| Mouse 3 | D-2 | 0.2 | 0.15 |
|  | D40 | 2.1 | 1.9 |
| Mouse 4 | D-2 | 0.25 | 0.1 |
|  | D40 | 0.2 | 0.2 |
| Mouse 5 | D-2 | 0.2 | 0.15 |
|  | D40 | 0.15 | 0.2 |
| Mouse 6 | D-2 | 0.3 | 0.1 |
|  | D40 | 0.1 | 0.25 |

These results show that the mice immunised with the kinoid produce antibodies capable of recognising the native protein and the kinoid in the same fashion. Furthermore, it confirms the non-toxicity of the immunisation with the kinoids as the mice tolerated the immunisation very well.

EXAMPLE 25

Treatment of the IL1 by Carboxymethylation 2 mg of IL1 was dissolved in 2 ml of 0.3 M Tris buffer, pH 8 containing 6 M guanidine and 10 mM dithiothreitol (DTT) previously deaerated by purging with nitrogen. 40 ml of a deaerated solution of 0.5 M iodacetic acid was added to this solution and the reaction mixture was incubated for 90 minutes at 37° C. under a nitrogen barrier. The reaction was then stopped by adding 10 ml of a 1:10 solution of P-mercaptoethanol. Incubation was extended for another hour and the reaction mixture was dialysed successively against 8 M, 4 M, 2 M urea and finally against PBS.

EXAMPLE 26

Loss of Biological Activity of the IL1 Treated by Carboxymethylation

The biological activity of IL1 (IL1 a or IL1) can be shown using cells from the NOB mouse line which are induced to produce IL2 in the presence of IL1. The cells are cultured in RPMI, 5% FCS. In the growth phase, they are washed (centrifugation-washing) and resuspended at a concentration of $10^5$ cells/ml. The cells are then aliquoted on microplates at 100 ml per well, 100 ml of IL1, native or treated according to example 25 is added to them in increasing dilutions. The plates are then incubated at 37° C. for 36 hours and the production of IL2 in the supernatant is measured by ELISA (Qantikine, R&D Diagnostics).

The results obtained (in optical density) for the IL1 and the kinoid of example 25 are the following:

| Quantity per well: | Native IL1 | Kinoid |
|---|---|---|
| 1 mg | 2.1 | 0.4 |
| 100 pg | 2.2 | 0.2 |
| 10 pg | 1.3 | 0.3 |
| 1 pg | 0.6 | 0.2 |
| 0.1 pg | 0.3 | 0.2 |
| control | 0.2 | 0.2 |

It is thus seen that the kinoid has lost its activity compared with the native IL1 by more than a factor of 1000.

EXAMPLE 27

Immunogenicity of the Carboxymethylated IL1

Kinoids prepared according to example 25 were used to immunise mice. The immunisation procedure is that which is traditionally used: injection into mice (in im), of 100 ml of emulsion (1:1) in Freund's complete adjuvant containing 20 mg of product at day 0, with a 5 mg Freund's incomplete adjuvant booster on days 21 and 35. The serum from the mice is sampled on days –2 and 40 and analysed by ELISA on plates sensitised with the native protein (not chemically treated) and with kinoid. The sera were tested at a dilution of 1/500.

The results expressed as optical density, obtained from 3 immunised mice (1 to 3) and 3 non-immunised mice (4 to 6), are given in the following table:

| | | Native protein | Kinoid |
|---|---|---|---|
| Mouse 1 | D-2 | 0.3 | 0.2 |
| | D40 | 1.6 | 1.7 |
| Mouse 2 | D-2 | 0.2 | 0.3 |
| | D40 | 1.8 | 2 |
| Mouse 3 | D-2 | 0.1 | 0.2 |
| | D40 | 1.9 | 1.6 |
| Mouse 4 | D-2 | 0.15 | 0.2 |
| | D40 | 0.1 | 0.25 |
| Mouse 5 | D-2 | 0.1 | 0.2 |
| | D40 | 0.3 | 0.3 |
| Mouse 6 | D-2 | 0.25 | 0.15 |
| | D40 | 0.3 | 0.1 |

These results show that the mice immunised with the kinoid produce antibodies capable of recognising the native protein and the kinoid in the same fashion. Furthermore, it confirms the non-toxicity of immunisation with kinoids as the mice tolerated the immunisation very well.

EXAMPLE 28

Inactivation of the IFNα by Maleimidation 50 of a 2 mg/ml solution of β-maleimidopropionic acid is added accompanied by stirring the same buffer, to 1.7 ml of a 1 mg/ml solution of IFNα in 30 mM buffer, 1 mM EDTA, pH 7.8. After reaction, for 15 minutes at laboratory temperature, the reaction mixture was dialysed against PBS.

The degree of inactivation of the maleimidated IFNα was evaluated by the test of inhibition of the lysis of the MDBK cells with the VSV virus (the same test as for IFNγ in example 2). The biological activity of the kinoid was inhibited by more than 99.9% compared with native IFNα.

EXAMPLE 29

Immunogenicity of the Maleimidated IFNα

Kinoids prepared according to example 28 were used to immunise mice. The immunisation procedure is that which is traditionally used: injection into mice (in im), of 100 ml of emulsion (1:1) in Freund's complete adjuvant containing 20 mg of product at day 0, with a 5 mg Freund's incomplete adjuvant booster on days 21 and 35. The serum from the mice is sampled on days −2 and 40 and analysed by ELISA on plates sensitised with the native protein (not chemically treated) and with kinoid. The sera were tested at a dilution of 1/500.

The results expressed as optical density, obtained from 3 immunised mice (1 to 3) and 3 non-immunised mice (4 to 6), are given in the following table:

| | | Native protein | Kinoid |
|---|---|---|---|
| Mouse 1 | D-2 | 0.1 | 0.25 |
| | D40 | 1.7 | 2 |
| Mouse 2 | D-2 | 0.15 | 0.15 |
| | D40 | 1.9 | 2.1 |
| Mouse 3 | D-2 | 0.35 | 0.3 |
| | D40 | 1.8 | 1.9 |
| Mouse 4 | D-2 | 0.15 | 0.1 |
| | D40 | 0.25 | 0.3 |
| Mouse 5 | D-2 | 0.1 | 0.3 |
| | D40 | 0.2 | 0.15 |
| Mouse 6 | D-2 | 0.25 | 0.1 |
| | D40 | 0.2 | 0.1 |

These results show that the mice immunised with the kinoid produce antibodies capable of recognising the native protein and the kinoid in the same fashion. Furthermore, it confirms the non-toxicity of immunisation with kinoids as the mice tolerated the immunisation very well.

What is claimed is:

1. A chemically modified TNF-α cytokine of formula $$Cy—(X—R)_n$$

in which Cy represents native TNF-α cytokine having toxic biological properties —(XR) represents a chemically-reactive function of an amino acid contained in said native TNF-α cytokine or where X represents an NH group or a sulphur atom, n represents an integer from 1 to 70, and R is either (i) a carboxymethylated, carboxamide, N-alkylmaleimide, thionitrobenzoic group or a radical formed by reaction of a thiol function with ammonium 4-chloro-7-sulphobenzofurazane, N-[iodoethyl]-trifluroacetamide or N-(6-[7-amino-4-methylcoumarin-3-acetamido]hexyl)-3'-(2'-pyridyldithio) propionamide; or (ii) a radical formed by reaction of an amino function with ethylacetimidate, an anhydride, 2-iminothiolane-HCl, N-succinimidyl S-acetylthioacetate, sulphosuccinimidyl-acetate, sulphosuccinimidyl-4-O-[4–4'-dimethoxytrityl]butyrate, succinimidyl 7-amino-4-methlcoumarin-3-acetate, sulphosuccinimidyl 7-amino-4-methylcoumarin-3-acetate or phenylglyoxal, said chemically modified TNF-α cytokine elicits antibodies which neutralize or block said native TNF-α cytokine and at the same time bringing about the loss of at least 90% of the toxic biological properties of said native TNF-α cytokine.

2. A chemically modified TNF-α cytokine according to claim 1, wherein at least 70% of the X groups are modified in the form of an —(XR) group.

3. A pharmaceutical composition, comprising as active ingredient the chemically modified TNF-α cytokine of claim 1 and a pharmaceutically acceptable excipient.

4. A pharmaceutical composition, comprising the chemically modified TNF-α cytokine of claim 1 in a therapeutic amount and a pharmaceutically acceptable excipient.

5. A vaccine, comprising the chemically modified TNF-α cytokine of claim 1.

6. The chemically modified TNF-α of claim 1 which is carboxyamidated TNF-α.

7. The chemically modified TNF-α cytokine of claim 1 which is ethylacetimidated TNF-α.

* * * * *